United States Patent [19]

Cheney

[11] Patent Number: 4,613,482

[45] Date of Patent: Sep. 23, 1986

[54] CONSTANT TEMPERATURE HEATING VALUE MEASUREMENT APPARATUS

[75] Inventor: M. Charles Cheney, Norfolk, Mass.

[73] Assignee: The Foxboro Company, Foxboro, Mass.

[21] Appl. No.: 564,791

[22] Filed: Dec. 23, 1983

[51] Int. Cl.[4] ............................................. G01N 25/22
[52] U.S. Cl. ........................................ 422/51; 374/33; 374/36; 436/147
[58] Field of Search ...................... 422/51, 94, 95, 78; 436/147, 155, 157; 374/33, 34, 36, 37, 38

[56] References Cited

U.S. PATENT DOCUMENTS

| 1,435,783 | 11/1922 | Aguillon | 374/36 |
| 2,836,482 | 5/1958 | Dreher | 422/78 X |
| 3,365,944 | 1/1968 | Hoagland et al. | 374/34 |
| 3,725,005 | 4/1973 | Innes | 436/147 |
| 4,329,873 | 5/1982 | Maeda | 422/95 X |
| 4,329,874 | 5/1982 | Maeda | 422/95 X |

FOREIGN PATENT DOCUMENTS

| 648159 | 7/1937 | Fed. Rep. of Germany | 374/36 |
| 2363605 | 12/1973 | Fed. Rep. of Germany | 436/147 |

Primary Examiner—Barry S. Richman
Assistant Examiner—Michael S. Gzybowski
Attorney, Agent, or Firm—William E. Meyer; Terrence Martin; Jack H. Wu

[57] ABSTRACT

An apparatus for determining the heating value of a fuel gas stream of variable composition utilizes a housing of high thermal conductivity defining a small volume combustion chamber, and filled with a bed of highly thermally conductive particles surrounding an electrical-resistance heater. The heater maintains the internal temperature of the chamber above the combustion point of the fuel gas, to totally combust the enclosed sample. The bed of particles transmits the heating effects of the combustion to the housing. A temperature sensor attached to the housing communicates with a feedback controller which acts to maintain the housing temperature constant, by appropriately adjusting the electrical energy supplied to the heater. Means are provided to correlate changes in the electrical energy to the heating content of the fuel sample.

18 Claims, 3 Drawing Figures

CONSTANT TEMPERATURE HEATING VALUE MEASUREMENT APPARATUS

The present invention relates in general to the field of devices for measuring the heating value (e.g., BTU's) of a fuel gas, and in particular to devices in which changes in the energy supplied to a heating source within a fuel gas reaction chamber provide an indication of the heating value.

Because of the ever-increasing costs of energy, utilization of the energy contained in the wild gas streams generated by many refining, metallurgical and chemical processes has become economically important. Uncontrolled fluctuations in the heating value of the material being combusted lead to gross inefficiencies in the combustion process, and may, in extreme circumstances, produce hazardous conditions or unacceptable variations in the characteristics of the products being manufactured.

To minimize these inefficiencies and waste, various control schemes have been introduced which attempt to monitor the fluctuations in the heating value of the fuel gases being introduced into a combustion chamber, and, via feedback mechanisms, to adjust the rate at which the fuel is introduced, so as to maintain delivery of a uniform heating value per unit time to the chamber. This is particularly important in the case of furnaces or boilers which combust a variety of fuel gases simultaneously, since at different times, the mix of fuel gases within a given volume may vary widely. Representative of such prior art control schemes is the apparatus shown in U.S. Pat. No. 4,329,873. This patent discloses an apparatus in which a sample gas and combustion gases are combined in a reaction chamber, and they are oxidized by the action of a catalytic heating element. This heating element is monitored for changes in its resistance caused by the heating of the combusted gases, and a feedback signal based on this resistance change controls the flow rate of the sample gas into the chamber. A similar system disclosed in U.S. Pat. No. 4,329,874 monitors the temperature difference between one end of a catalytically-coated heating element located within the reaction chamber and the opposite end located outside the chamber. The end of the heating element within the reaction chamber is heated by the oxidation of the fuel gas, however, a controller varies the current to the element to maintain a predetermined temperature differential between its two ends. The measure of the difference in the electric current supplied to the element can be correlated to the calorific heating content of the fuel gas.

In U.S. Pat. No. 4,170,455, there is shown a system in which the temperature of an incoming fuel gas is measured. The gas is passed through a perforate metal heat shield into contact with a bed of particulate catalyst, thereby causing combustion. The temperature of the combusted gas is measured, with the temperature difference being correlatable to the concentration of the gas of interest. The assembly formed of the particulate catalyst and the surrounding metal mesh screen is configured to maximize the bed volume-to-surface area ratio, so as to maximize the flow capacity-to-heat loss ratio of the system.

A major drawback of many such prior art systems is that, since they are based on a catalytic reaction and localized temperature measurement, the response of the system is inherently dependent on the composition of the fuel gases. Catalysts are generally not of universal applicability, and the rate of catalytic reactions varies greatly for different reacting substances. Therefore if a combustion process utilizes fuel gases of a widely varying nature, separate measurement systems using separate catalysts and/or calibrations would be required. When the composition of the fuel is unknown, the design of the measuring unit must take into account the highly variable rates of oxidation of the component gases, which may range from hydrogen (very reactive) to methane and other alkanes. Any heat value measurement derived from the heat released by combustion of only part of the sample is probably composition dependent, as the fraction which will react depends on the chemical species present and the stoichiometry of the mixture.

It should be pointed out that catalysts are susceptible to "poisoning" when contaminated by foreign substances, which often are an unavoidable part of the incoming fuel stream. Also, catalysts tend to age, and their performance characteristics change over time, thereby adversely affecting the accuracy and precision of the control process.

Therefore, there is still a need within the industry to provide a more universal measuring apparatus for measuring the BTU, or heating value or calorific content, of a fuel gas, which is capable of measuring a wide variety of sample gases, either individually or in mixtures, and without recalibration.

It is a further object of the present invention to provide such a system which is not susceptible to poisoning or degradation by foreign fuel gases, and is tolerant of wide fluctuations in the type of fuel gas being supplied.

It is a further object of the present invention to provide an apparatus to perform the above functions in a manner that is adaptable to existing furnaces, boilers and other similar combustion apparatus, and which performs its functions in an economical manner.

A fuel gas heating value measuring apparatus in accordance with the present invention comprises a combustion unit, including an outer shell having a high coefficient of thermal conductivity, forming an inner combustion chamber. Fuel gas and oxidizing gas inlets communicate with the interior of this combustion chamber. A heating element positioned within the combustion chamber maintains the chamber at a temperature above the combustion temperature of any of the constituents of the fuel gas, with a source of energy provided for the heating element. The apparatus includes a mechanism for achieving complete combustion of the fuel gas within the combustion chamber by the heating element, while also transmitting the heating effects of the combustion uniformly to the outer shell. A temperature sensor applied to the outer shell produces an output signal corresponding to the sensed temperature, and provides this signal to a mechanism for varying the amount of energy supplied by the energy source to the heating element in response to the output signal, so as to maintain the temperature of the outer shell constant. Finally, a mechanism is provided for measuring the variation in energy supplied by the energy source and correlating this variation to the heating value of the fuel which has been combusted.

In a particular embodiment of the present invention, the mechanism for achieving the complete combustion of the fuel gas is a tightly compacted bed or aggregate of particles, having a high thermal conductivity, such as alumina, beryllia or silver. These particles are densely packed within a combustion chamber having a relatively small internal volume. The fuel gas is injected into one end of the chamber, upstream of the oxidizing gas. This initially produces a stratified, i.e., non-homogeneous, mixing of the fuel and the oxidizing gas (a "rich" mixture) which facilitates the ignition of the fuel gas. Subsequent diffusion of the fuel and oxidizing gases through the bed of particles results in complete mixing of the gases and effects total combustion of the fuel gas, i.e., a release of the total chemical energy content of the fuel gas. Because of the intimate contact among the particles of the bed and their high thermal conductivity, the totality of the heating effects caused by combustion at any point within the chamber is immediately transmitted to the outer highly conductive thermal shell, and is distributed evenly throughout the surface of the shell. In effect, the bed of particles surrounding the heating element acts as an extension of the heating element, producing, as it were, a widely distributed heating element.

Because of the near instantaneous transfer of the total heating effect to the outer shell, and the uniform temperature distribution across the shell surface, every point on the surface is theoretically an indicator of the thermal effect due to the combustion of the fuel gas. Therefore the temperature at any arbitrary point on the surface can be correlated to the heat content of the gas which has effected the sensed change in temperature.

The numerous operating features and advantages of the present invention will be made clear by the following detailed description, in conjunction with the accompanying drawings in which.

Figure 1:
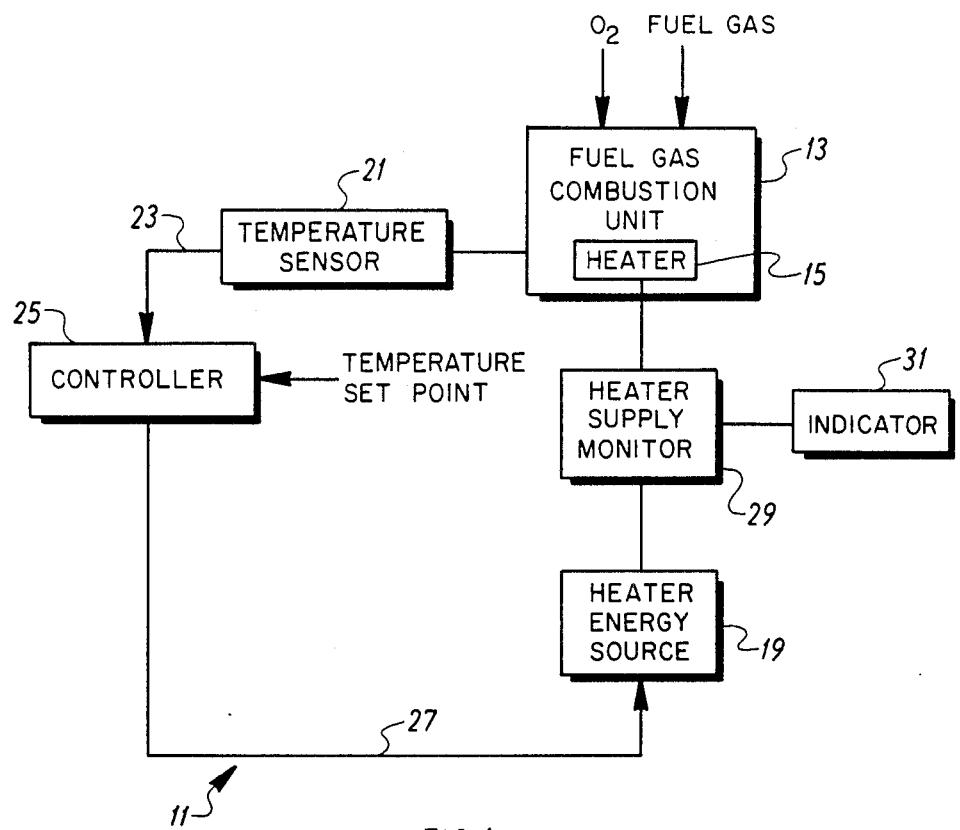
FIG. 1 is a schematic, in block diagram form, depicting a measuring apparatus built in accordance with the present invention.

Referring now to FIG. 1, a fuel gas heating value measuring apparatus in accordance with the present invention, depicted generally by reference numeral 11, includes a fuel gas combustion unit 13, to be described in further detail hereinafter. The function of the combustion unit is to combine the sample gas containing combustible constituents (e.g., hydrogen, methane, carbon monoxide) and an oxidizing gas (e.g., air or oxygen) to achieve total combustion of the fuel gas. A heater 15, located within the combustion unit, and heated to a temperature above the normal combustion point of the fuel gas in question, initiates the oxidizing reaction. The total heating effects achieved by the combustion as well as the output of the heater are transferred to the outer surface of the combustion unit, the temperature of which surface is to be maintained at a constant, predetermined level.

This surface temperature is a function not only of the amount of heat generated by the heater 15 itself, but also of the heat generated by the combustion of the fuel gas and the oxygen. Naturally, as the heating value or calorific content of the fuel gas varies, the amount of heating effect produced by combustion of this fuel gas changes accordingly. Therefore, in order to maintain the surface temperature constant, the amount of heat provided by the heater must change inversely with changes in the heating value of the gas, i.e., more heat being required from the heater when the heating value of the gas decreases, and less heat required from the heater when the heating value increases. The operation of the heater 15 is controlled by the amount of energy supplied to the heater from an external energy source 19, with more or less energy being supplied to the heater as appropriate. The temperature of the outer surface is monitored by a conventional temperature sensor 21, such as a thermocouple or resistance-temperature device (RTD), securely fastened thereto. The output signal from this temperature sensor, directed along a line 23, is fed into a conventional feedback controller 25. Representative of such a conventional controller is the SPEC 200 electronic analog controller manufactured by The Foxboro Company, Foxboro, Mass., assignee of the present application. As the actual temperature sensed by the temperature sensor deviates from a temperature set point programmed into the controller, the controller, in a well-known conventional manner, generates an error signal. This signal is fed back along a line 27 to the heater energy source 19, to appropriately modify the amount of energy supplied to the heater 15 and counteract the increase or decrease in surface temperature produced by the internal combustion of the fuel gas. In the depicted embodiment, the heater is a resistance wire (see also FIG. 2), and the energy being supplied thereto is in the form of an electrical current. A typical such resistance wire is one formed of a 60 percent nickel, 24 percent iron and 16 percent chromium alloy, sold under the trade name Nichrome. However, the present invention can operate effectively with a wide variety of conventionally known heaters, powered by electrical or non-electrical sources. A monitoring device 29, interposed between the combustion unit heater and the heater energy source measures the variation in the energy supplied to the heater. The difference between the electric power required with and without fuel gas flow equals the heating value supplied by the fuel. An indicator 31, whose input is derived from the monitoring device, provides a direct indication of the heating value of the fuel gas in question, its scale having been appropriately calibrated to the proper units of measurement (e.g., BTU per unit volume).

Figure 2:
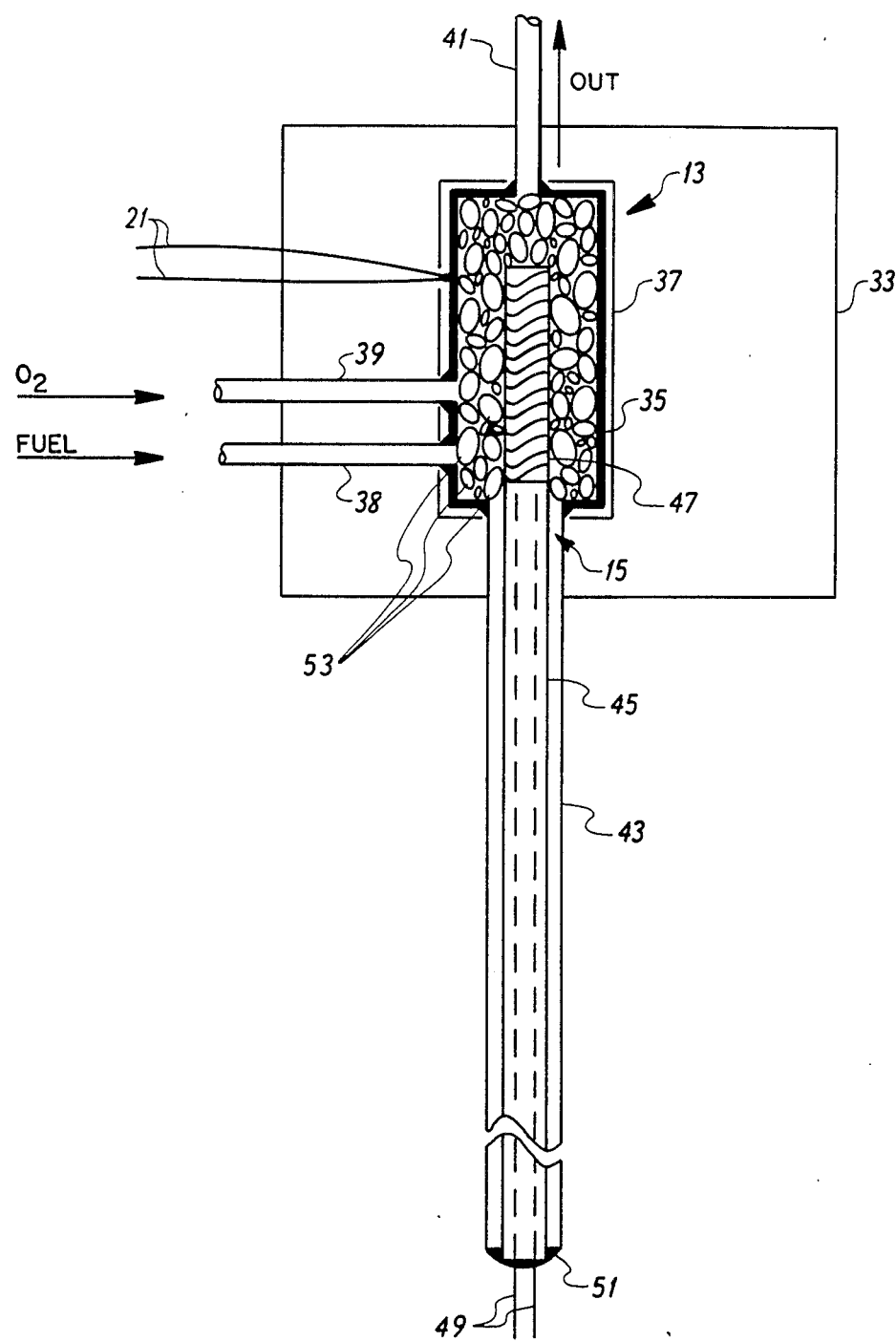
FIG. 2 is an elevation view, in section, of the fuel gas combustion unit shown in FIG. 1.

Referring now to FIG. 2, the specific combustion unit 13 for achieving efficient combustion of the fuel gas is shown in greater detail. The entire combustion unit is enclosed with a hermetically sealed metal jacket 33, which is evacuated so as to thermally insulate the combustion unit from its surroundings in order to limit the total amount of power required to maintain it at the desired operating temperature. Such insulation also may be achieved, e.g., by enclosing the combustion unit in a guard heater held at some elevated temperature below the desired operating temperature. The outer shell 35 of the combustion unit, which defines an interior combustion or reaction chamber, is made of a material having a high thermal conductivity, for example, silver. A shiny platinum foil 37 (which does not tarnish at elevated temperatures) is tightly wrapped about the outer shell to reduce radiative heat loss. This type of construction produces an overall device that is isothermal and which has a constant and controllable rate of heat loss to its surroundings.

The outer shell 35 is penetrated by two inlet lines, 38, 39, the first of which delivers the fuel gas sample to be measured, while the other delivers the oxygen. The interface between these inlet lines and the outer shell are securely brazed, welded or similarly bonded to insure a gas-tight construction. There is also an exhaust line 41 similarly attached to the outer shell and communicating with the combustion chamber for exhausting the combustion products. An inlet conduit 43 provides access for the heating element 15, comprising an alumina (Al$_2$O$_3$) support member 45 with a resistance wire 47 wrapped around the exterior of the alumina member at its upper end. A pair of electrical leads 49 connected to the resistance wire passes through the interior of the alumina support and out through its bottom end via a gas seal such as epoxy or a ceramic material which prevents the gaseous content of the chamber from exiting the chamber except through exhaust line 41.

Filling the entire remaining volume of the combustion chamber is a compacted bed of particles 53 having a high coefficient of thermal conductivity. These particles surround the heater 15 and are in intimate contact with the heater and each other. Typical particle materials usable in the present invention are beads of silver, alumina, or beryllia (Be$_2$O$_3$). In the specific embodiment shown, these particles are of alumina, having a size distribution of 8–20 mesh. The intimate contact of the particles with both the heater 15 and the outer shell 35, as well as with each other, insures that localized heating effects occurring anywhere within the combustion chamber are almost instantaneously transferred to all parts of the combustion unit, including the outer surface of the silver shell. This rapid transfer is aided by the relatively small internal volume of the combustion unit, typically 2.5 cm$^3$. In essence, then, the highly thermally conductive configuration of the combustion unit achieves an integrating effect, in that the temperature of the outer shell is a function of the sum total of the heating effects throughout the combustion chamber. The temperature sensor is securely bonded to the silver shell through a hole in the foil 37. Placement of the sensor is not critical, because the temperature is uniform across the entire outer surface 35, a direct result of the optimum thermal conductivity of the combustion unit as a whole.

In operation the fuel gas is introduced at the lower end of the combustion unit 13, with the oxidizer being introduced at a higher point, downstream of the fuel gas. This condition makes the initially formed gas mixture fuel-rich and, as is well known, enhances the ability of the fuel gas to be ignited. The passage of the two gases through the many circuitous paths within the bed of alumina particles 53 produces a turbulent interaction, to achieve a thorough mixing of the fuel gas and the oxygen, which produces complete combustion of the fuel gas. Also, the bed of highly thermally conductive particles effectively operates as an extension of the resistance wire heater, by achieving a more widely distributed heating surface, and further facilitating complete combustion. Many prior art devices, which depend on combustion of only a portion of the total fuel gasoxidizer sample mixture, require a separate calibration for different sample compositions because the temperature profile generated by heat of combustion will depend on the reactivity of the fuel gas species. However, such recalibration is not required within the present invention, because of the previously mentioned integrating effect. Rather, the total combustion, and the high thermal conductivity of the overall construction combine to achieve an accurate characterization of the gas sample's heating value, regardless of the reactivity of the gas.

It should be pointed out that although the terms "complete combustion" and "total combustion" are used herein to distinguish the mode of operation of the present invention from prior art devices which use only sampling techniques, this is not to say that the present invention will not function with anything less than 100 percent combustion of the fuel gas. The consequence of less than 100 percent combustion is a corresponding loss in accuracy. For example, if only 99 percent of the total fuel gas sample combusts, the accuracy of the heating value measurement will not be better than one percent.

The actual combustion of the fuel gas and the oxygen is initiated by the heated resistance wire 47. Unlike prior art catalytic combustion devices as discussed above, which operate at a temperature below the normal combustion point of the sample gases, the resistance wire is heated to raise the temperature of the chamber above the combustion point of any of the constituent elements within the fuel gas. As mentioned above, the electric current supplied to the resistance wire varies, depending on the heating value of the fuel gas being combusted. Assuming there is a known, constant rate of fuel gas flow for the duration of the measurement, the magnitude of the change in the number of watts of electrical power consumed is equivalent to the heating power (e.g., in BTU's) of the fuel gas sample. This change in electrical power is detected by using a conventional wattmeter as the monitoring device 29.

Figure 3:
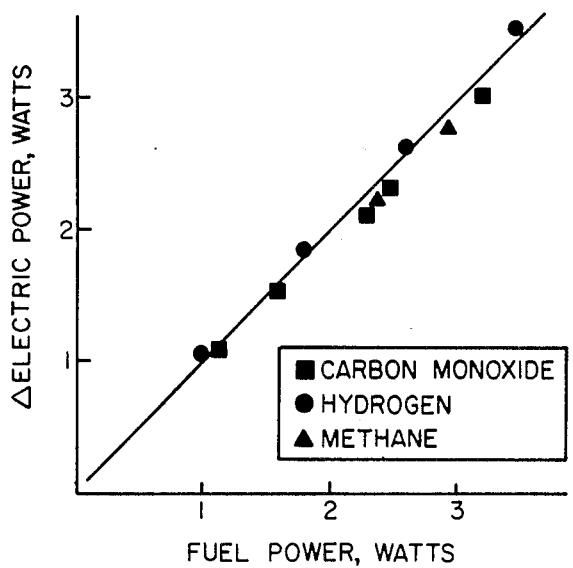
FIG. 3 is a graph showing the correlation of fuel power versus electrical power supplied to the heater, for a variety of fuel gases.

Experiments with devices such as the above described embodiment, using pure fuel gases such as H$_2$, CO and CH4 have yielded efficiencies of 97 to 100 percent, with a response time of about twenty seconds. The graph of FIG. 3 clearly depicts the wide applicability of the present invention, by showing the equivalence of fuel power to changes in electrical power for these three gases. These actual measurements were made without the need for any recalibration after changes in the species being measured.

Instead of the measured heating value of the fuel gas being merely displayed on the indicating device 31, the heating value information can be fed back to a supply valve (not shown) governing the rate of flow of the fuel gas to a furnace or similar combustion apparatus, to continuously deliver a constant heating value per unit time thereto. By maintaining a constant heating value input, the furnace output similarly can be maintained constant.

Similar results are achieved by directly varying the amount of fuel gas supplied to the combustion unit 13 to maintain the constant temperature at the outer shell 35, rather than by varying the electric current to the heater wire 47. In this situation, the same signal which controls the gas supply to the combustion unit is used to control the gas supply to the main burner or furnace, so that the present invention functions as a set point controller, rather than a mere heating value indicator.

Although the particles 53 are chosen primarily for their high thermal conductivity, it is recognized that, in the case of certain fuel gases, there may be an attendant amount of catalytic action. However, as discussed above, the present invention is not intended to require a catalytic reaction. The fact that the particle material is not a catalyst allows the present invention to be applied to a wide variety of fuel gases, while avoiding the common problem of poisoning catalysts by sulfides, lead compounds, etc.

Although the above embodiment has been described in quite specific terms, it is understood that certain modifications may become apparent to those skilled in the art. For example, materials other than silver may be usable for the outer shell of the combustion unit, such as for example palladium which has high thermal conductivity but a far higher melting point than silver. Also, at higher operating temperatures it may be unnecessary to use oxygen as the oxidizing agent, and normal atmospheric air may be sufficient. Nevertheless, it is intended that these and other similar modifications be included within the scope of the following appended claims.

I claim:

1. Apparatus for measuring the heating value of a fuel gas, when combusted with an oxidizer gas, comprising:
   a combustion unit, including
      an outer shell having a high coefficient of thermal conductivity, defining an inner combustion chamber,
      a fuel gas conduit communicating with said combustion chamber to provide a fuel gas thereby,
      an oxidizer gas conduit communicating with said combustion chamber to provide an oxidizer gas thereby,
      a heating element within said combustion chamber for raising the temperature of said combustion chamber above the combustion temperature of said fuel gas;
   means for supplying energy to the heating element;
   means within said combustion chamber defining a path for conducting and mixing said fuel gas with said oxidizer gas to achieve substantially complete combustion of said fuel gas with said oxidizer gas within the combustion chamber, and for transmitting substantially the total heating effects within said combustion chamber to said outer shell;
   means for sensing the temperature of the outer shell and producing an output signal corresponding to the temperature of the outer shell;
   means, responsive to said temperature output signal, for maintaining the temperature of the shell constant; and
   means, in communication with said temperature maintaining means, for relating the response of said temperature maintaining means to a measure of the heating value of said fuel gas.

2. The apparatus as set forth in claim 1, wherein said oxidizer gas conduit is located downstream of said fuel gas conduit to yield a stratified mixture of said fuel gas and said oxidizer gas.

3. The apparatus as set forth in claim 1, wherein said means for maintaining the temperature comprises means for varying the rate at which said fuel gas is introduced into said combustion chamber.

4. The apparatus as set forth in claim 3, wherein means for varying the rate at which said fuel gas is introduced into said combustion chamber comprises:
   a valve in fluid communication with said fuel gas conduit; and
   a feedback controller, responsive to said temperature output signal and coupled to said valve.

5. The apparatus as set forth in claim 1, further comprising means for controlling the rate of heat loss from said combustion unit.

6. The apparatus as set forth in claim 5, wherein said means for controlling the rate of heat loss comprises a platinum foil sheathing surrounding said outer shell.

7. The apparatus as set forth in claim 6, wherein said means for controlling the rate of heat loss further includes a hermetically sealed, evacuated chamber surrounding said combustion unit.

8. The apparatus as set forth in claim 1, wherein said means of achieving substantially complete combustion comprises an aggregate of particles of high thermal conductivity, filling said combustion chamber and surrounding said heating element.

9. The apparatus as set forth in claim 8, wherein said particles are beryllia.

10. The apparatus as set forth in claim 8, wherein said particles are silver.

11. The apparatus as set forth in claim 8, wherein said particles are alumina.

12. The apparatus as set forth in claim 11, wherein said particles have a size distribution in the range of 8-20 mesh.

13. The apparatus as set forth in claim 1, wherein said means for maintaining the temperature comprises means for varying the amount of energy supplied by a source of energy to said heating element.

14. The apparatus as set forth in claim 13, wherein said means for varying the amount of energy supplied by said source of energy to said heating element comprises a feedback controller coupled to said source of energy.

15. The apparatus as set forth in claim 13, wherein said heating element comprises a resistance heater, and said source of energy comprises a source of electrical energy.

16. The apparatus as set forth in claim 15, wherein said resistance heater comprises a wire made of a nickel, iron and chromium alloy.

17. The apparatus as set forth in claim 15, wherein said means for relating the response of said temperature+ maintaining means to the heating value of said fuel gas comprises an electric power meter interposed between said resistance heater and said source of electrical energy, and means for equating changes in said electric power to the heating value of said fuel gas.

18. Apparatus for measuring the heating value of a fuel gas, when combusted with an oxidizer gas, comprising:
   a combustion unit, including
      an outer shell having a high coefficient of thermal conductivity, defining an inner combustion chamber,
      a platinum foil sheath surrounding said outer shell,
      a fuel gas conduit communicating with said combustion chamber to provide a fuel gas thereby,
      an oxidizer gas conduit communicating with said combustion chamber to provide an oxidizer gas thereby,
      a resistance heater within said combustion chamber, for raising the temperature of said combustion chamber above the combustion temperature of said fuel gas, and
      an aggregate of particles of high thermal conductivity filling said combustion chamber and surrounding said resistance heater, said particles serving to mix said fuel gas and said oxidizing gas to facilitate complete combustion thereof and to transmit the heating effects within said combustion chamber to said outer shell;
   a source of electric power for supplying electrical power to said resistance heater;
   means for sensing the temperature of the outer shell and for producing an output signal corresponding to the temperature of the outer shell;
   a controller means for varying the amount of electric power supplied to said resistance heater by said source of electric power in response to said output signal, to maintain the temperature of said outer shell constant; and
   means for relating the variation in said electric power to a measure of the heating value of said fuel gas.

* * * * *